United States Patent [19]

Hart et al.

[11] Patent Number: 5,223,490
[45] Date of Patent: Jun. 29, 1993

[54] REVERSE TRANSCRIPTASE INHIBITORS FOR TREATING ADENOCARCINOMAS

[75] Inventors: Charles A. Hart, Wirral; Kevin McCarthy, Liverpool; Samuel J. Leinster; Christopher D. Green, both of Wirral, all of Great Britain; Ayad M. Al-Sumidaie, Baghdad, Iran

[73] Assignee: University of Liverpool, Liverpool, United Kingdom

[21] Appl. No.: 536,669

[22] PCT Filed: Jan. 6, 1989

[86] PCT No.: PCT/GB90/00010
§ 371 Date: Jul. 5, 1990
§ 102(e) Date: Jul. 5, 1990

[87] PCT Pub. No.: WO89/06132
PCT Pub. Date: Jul. 13, 1989

[30] Foreign Application Priority Data

Jan. 7, 1988 [GB] United Kingdom ............... 8800276

[51] Int. Cl.⁵ ............................................. A61K 31/70
[52] U.S. Cl. ........................................ 514/50; 514/934
[58] Field of Search ........................... 514/49, 50, 934

[56] References Cited

FOREIGN PATENT DOCUMENTS 0199451 10/1986 European Pat. Off. .
0216510 4/1987 European Pat. Off. .

OTHER PUBLICATIONS

R. Robins Pharm. Res. No. 1 1984 pp. 11-17.
R. Michalides, et al., Can. Res. 35:1003-1008, 1986.
S. Spiegelman, Cancer Chemotherapy Reports, Pt 1, 58(4):595-613, 1974.
J. Moslier, et al., Biochem & Biophy Res. Communications 139(3):1071-1077, 1986.
J. Balzarini, et al., BBRC, 136(1):64-71, 1986.
E. De Clercq, Antican. Res. 7:1023-1038 1987.
D. Chalbos, et al., J. Gen. Virol. 62:65-80, 1982.
J. Balzarini, et al., FEBS Lett. 185(1):95-100, 1985.

*Primary Examiner*—John W. Rollins
*Attorney, Agent, or Firm*—Wenderoth, Lind & Ponack

[57] ABSTRACT

A reverse transcriptase inhibitor such as 3'-azido-3-deoxythymidine is used for the treatment or prophylaxis of a retrovirus-associated carcinoma such as breast cancer in a human.

5 Claims, No Drawings

REVERSE TRANSCRIPTASE INHIBITORS FOR TREATING ADENOCARCINOMAS

The present invention is concerned with materials and processes for the treatment of human adenocarcinomas, particularly breast carcinoma.

Breast carcinoma is known to affect about 9% of women in the Western World, and in women aged between 40 to 54 years it is the major cause of death.

Monocytes from patients with breast cancer show depression of both directional and random migration, and lower phagocytic activity compared with those obtained from control subjects. This dysfunction is associated with giant-cell formation when such cells are incubated for 6 days. Virus-induced cell fusion is a possible means of giant-cell formation. Giant-cell formation can be induced in normal monocytes by incubation with a 220 nm filtrate of cytosol or a similar filtrate of cell-free culture medium (CFCM) obtained from the incubated monocytes from patients with breast cancer. These observations strongly suggest that monocytes from patients with breast cancer contain a factor that has the ability to induce giant-cell formation by monocytes from normal controls.

In mice, the development of one particular form of mammary tumour depends on the presence of a retrovirus, murine mammary tumour virus (MMTV). Some homology has been reported between proviral DNA sequences of MMTV and the human genome, and one suggestion has been that the homology is due to the presence of an as yet unidentified latent retrovirus in certain human tissues. The human breast cancer cell line (T471) has been reported to contain a gene sequence (9 kb long) that has a homology with part of the genome of MMTV. These findings have reawakened old speculation that human breast cancer may have, at least in part, a viral aetiology.

Recently some very specific anti-viral materials have become available. These are zidovudine (also referred to as "AZT" and chemically 3'-azido-3'-dexoythymidine), dideoxyadenosine ("DDA"), dideoxycytidine ("DDC") and phosphoformate ('Foscarnet'). They all have the specific property of inhibiting the reverse transcriptase enzyme of retroviruses, and thus could be used to determine whether such enzyme is present and hence to establish specifically the presence of retroviral entities.

It has now been found that monocyte cells in human breast cancer do indeed contain at least one retroviral reverse transcriptase. Furthermore it has now been found that retroviral activity is present in cells other than monocytes and that it can be transmitted from cell to cell. It has moreover also been found that the activity of such, and therefore of the retroviruses themselves, can be inhibited by the use of zidovudine and close derivatives and congeners thereof.

According to the present invention we provide the use of a reverse transcriptase inhibitor or a pharmaceutically acceptable derivative thereof in the manufacture of a medicament for the treatment or prophylaxis of retrovirus-associated adenocarcinoma in a human; and/or the treatment or prophylaxis of a human retrovirus infection associated with adenocarcinoma in a human.

According to further features of the present invention we provide:

a) a method for the treatment or prophylaxis of retrovirus-associated adenocarcinoma in a human which comprises the administration of reverse transcriptase inhibitor or a pharmaceutically acceptable derivative thereof to the human in an amount effective to treat said adenocarcinoma;

b) a method for the treatment or prophylaxis of a retrovirus infection associated with adenocarcinoma in a human which comprises administering to the human a reverse transcriptase inhibitor or a pharmaceutically acceptable derivative thereof in an amount effective to treat or inhibit said retrovirus infection; and c) a method of alleviating the symptoms of a retrovirus-associated human adenocarcinoma which comprises the administration of a reverse transcriptase inhibitor or a pharmaceutically acceptable derivative thereof to the human in amount effective to alleviate said symptoms.

The present invention also includes a method for the identification of retrovirus-associated human adenocarcinoma which comprises bringing a biological sample of, or derived from, human tissue into contact with an agent adapted for the identification of retrovirus.

A method for the identification of retrovirus-associated human adenocarcinoma which comprises bringing a biological sample of, or derived from, human tissue into contact with an agent adapted for the identification of retroviral reverse transcriptase.

With regard to the above-described treatment of a retrovirus associated with adenocarcinoma, the present invention includes specifically the inhibition of the reverse transcriptase of the said retrovirus.

It will be understood that any known reverse transcriptase inhibitor may be used in accordance with the present invention. Furthermore it will be understood that the present invention also provides for the use of more than one reverse transcriptase inhibitor either simultaneously or in conjunction. Examples of reverse transcriptase inhibitors include 3'-azido-3'-deoxythymidine and other 3'-azido purine or pyrimidine nucleosides, for example as described in EP 217580 (Wellcome) 2',3'-dideoxy purine nucleosides such as 2',3'-dideoxy-2-amino-purine, 3'-fluoronucleosides such as 3'fluoroguanosine, carbocyclic nucleosides such as carbovir, 2',3'-dideoxy-2',3'-didehydro nucleosides such as 2',3'dideoxy-2',3'-didehydrothymidine, and ribavirin.

A preferred inhibitor of reverse transcriptase is 3'-azido-3'-deoxythymidine.

The present invention is particularly useful in relation to human breast carcinoma.

According to a specific embodiment of the present invention we provide.

The use of 3'-azido-3'-deoxythymidine or a pharmaceutically acceptable derivative thereof in the manufacture of a medicament for the treatment or prophylaxis of breast carcinoma in a human; and/or the treatment or prophylaxis of a human retrovirus infection associated with breast carcinoma in a human.

The term "pharmaceutically acceptable derivative" is used herein to denote a physiologically functional equivalent of 3'-azido-3'-deoxythymidine and includes any pharmaceutically acceptable salt or ester (or salt of such ester) of 3'-azido-3'deoxythymidine or any other compound which, upon administration to a human subject, is capable of providing (directly or indirectly) 3'-azido-3'-deoxythymidine or an antiretrovirally active metabolite or residue thereof. Thus, for example, it is understood that 3'-azido-3'-deoxythymidine is phosphorylated in vivo successively to the monophosphate, the diphosphate and finally to the triphosphate ester which acts as an inhibitor of the reverse transcriptase of the retrovirus which has been identified in association with breast carcinoma.

Preferred esters of 3'-azido-3'-deoxythymidine include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); and mono-, di- or tri-phosphate esters. With regard to the above-described esters, unless otherwise specified, any alkyl moieties present in such esters advantageously contain 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Examples of pharmaceutically acceptable salts of 3'-azido-3'-deoxythymidine and its pharmaceutically acceptable derivatives include base salts, e.g. derived from an appropriate base, such as alkali metal (e.g. sodium), alkaline earth metal (e.g. magnesium) salts, ammonium and $NX^+_4$ (wherein X is $C_{1-4}$ alkyl).

3'-azido-3'-deoxythymidine, or a pharmaceutically acceptable derivative thereof (hereafter referred to as the active ingredient), may be administered to humans in accordance with the invention by any suitable route including oral, rectal, nasal, topical (including buccal and sublingual), vaginal and parenteral (including subcutaneous, intramuscular, intravenous, intradermal, intramammary, intralesional, intrapleural, intraperitoneal, intrathecal and intra-arterial, and into lymphatic vessels or nodes and to bone or bone marrow).

In general a suitable dose will be in the range of 3.0 to 120 mg per kilogram body weight of the patient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form. Convenient unit dosage forms contain 250 mg or 500 mg of active ingredient. The dosage used will be at the discretion of the physician and will vary according to the route of administration, the nature and severity of the condition, the immune state and age of the patient, the nature of the active ingredient, and whether it is used for prophylaxis or treatment.

Experiments with 3'-azido-3'-deoxythymidine suggest that a dose should be administered to achieve peak plasma concentrations of the active compound of from about 1 to about 75 um, preferably about 2 to 50 um, most preferably about 3 to about 30 um. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continous infusion to provide about 0.01 to about 5.0 mg/kg/hour or by intermittent infusions containing about 0.4 to about 15 mg/kg of the active ingredient.

The active ingredients disclosed herein, including 3'-azido-3'-deoxythymidine, may also be used in the identification, treatment, prophylaxis, inhibition, alleviation or suppression of other solid tumours, including adenocarcinomas and carcinomas of humans associated with retroviral infections.

While it is possible for the active ingredient to be administered alone, it is preferable to present it as a pharmaceutical formulation. Such formulations comprise at least one active ingredient, as above-defined, together with one or more acceptable carriers thereof and optionally other therapeutical agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. Oral formulations may further as sweeteners, flavouring agents and thickners.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatine, hydroxypropylmethyl cellulose), lubricant, inert diluent, preservative, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored.

The above formulations may be formulated so as to provide slow or controlled release of the active ingredient therein using, for example, hydroxypropylmethylcellulose in varying proportions to provide the desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above receited, or an appropriate fraction thereof, of an active ingredient.

Specific examples of the above pharmaceutical formulations are described in European Patent Specification No. 196185 which is herein incorporated by reference.

In addition to 3'-azido-3'-deoxythymidine and its pharmaceutically acceptable derivatives, the present invention also relates to other known retroviral reverse transcriptase inhibitors including: phosphonoformic acid, 2',3'-dideoxynucleosides such as 2',3'-dideoxycytidine, 2',3'-dideoxyadenosine, 2',3'-dideoxyinosine, and 2',3'-dideoxyguanosine.

In accordance with the present invention any such additional reverse transcriptase inhibitor may be employed in place of or in addition to 3'-azido-3'-deoxythymidine in the above-described embodiments of the invention.

The scope and significance of the present invention is more fully indicated in greater detail, but by way of example only, in the following experimental details:

EXAMPLE 1

Methods

Patients and Controls

Monocytes from 32 women with early breast cancer and from 27 healthy age-matched female volunteers with no evidence or family history of breast disease were studied. Neither patients nor controls were receiving any form of medication at the time of study. Diagnosis of breast cancer was based on needle biopsy preoperatively and confirmed on histological examination of the excised tumour.

Monocyte Separation

Peripheral blood monocytes from patients and controls were collected and purified over Ficoll-Hypaque and a discontinous Percoll density gradient. See, for example, Al-Sumidiae et al., "Characterisation of the under agarose method for quantifying migration of highly purified human monocytes", Journal of Immunological Methods, 1984, 75 129–40.

Preparation of Cell-free Culture Medium (CFCM)

1 million monocytes from patients and controls were suspended in Eagle's medium supplemented with 10% fetal calf serum and 15 $\mu$mol/1 5'-azacytidine. After 6 days' incubation at 37° C. in 5% carbon dioxide, in air, in a humidified incubator, the supernatant was filtered through a 220 nm filter. The filtrates were centrifuged at 100000 g for o1 hour at 4° C. The pellets were suspended in 1 ml of TNE buffer pH 8.3 (10 mmol/1 "tris" - HCl, 150 mmol/1 NaCl, 2 mmol/1 edetic acid) for reverse transcriptase assay or in 2% phosphotungstic acid for electron microscopy.

Reverse Transcriptase Assay

Reverse transcriptase activity was detected by the incorporation of radiolabelled deoxycytidine triphosphate (dCTP) into DNA in the presence of a synthetic RNA template. The standard method and template (polyguanylic acid) described by Green et al., "RNA directed DNA polymerase", Prog. Nucl. Acid Res. Mol. Biol., 1974, 14, 202–334 was used.

To ensure release of RT activity from presumtive retrovirus particles, the high-speed pellet was suspended in 'Nonidet P 40' (0.2%, v/v) and 50 $\mu$mol/1 dithiothreitol (DTT) and incubated at 20° C. for 15 min. The assay reaction mix contained, in a final volume of 100 $\mu$l, 45 $\mu$l of sample, 5 $\mu$mol "tris" - hydrochloric acid pH 8.3, 5 $\mu$mol potassium chloride, 2.5 $\mu$mol DTT, 0.6 $\mu$mol magnesium chloride, 0.16 $\mu$mol each of deoxyadenosine triphosphate, deoxythymidine triphosphate, and deoxyguanosine triphosphate, 0.05 $\mu$mol dCTP, 5 $\mu$Ci (alpha-$^{32}$P) dCTP (3000 ci/mmol), 0.5 $\mu$g oligodeoxycytidylic acid (oligo d(pC) 8), and 0.5 $\mu$g polyguanylic acid. The reaction was incubated at 37° C. for 2 hours. Background incorporation was determined any substituting 45 $\mu$l of TNE (preincubated with Nonidet P40 DTT) for the sample in the reaction mixture. The reaction was stopped by the addition of 0.4 ml of 10% (w/v) trichloracetic acid (TCA) and 25 $\mu$g of calf thymus DNA as carrier. The DNA was precipitated overnight at $-20°$ C. The precipitated radioactivity was collected by filtration onto a GF/C glass-fibre filter and washed with 50 ml of 5% (w/v) TCA. The radioactivity on the filter was measured in a scintillation counter.

Sucrose Gradient

A discontinuous density gradient of 20, 30, 40 and 60% sucrose in TNE was prepared and allowed to stand at 20° C. for 2 hours. This produced a range of densities (1.1–1.28 g/ml) which span the known buoyant densities (1.16–1.18 g/ml) of retroviruses. A high-speed pellet was prepared from CFCM of incubated monocytes from patients with breast cancer as described above. The pellet was either disrupted by the addition of the non-ionic detergents Nonidet P40 and DTT or resuspended with NE buffer and incubated at 20° C. for 15 minutes before being layered onto the gradient which was then certrifuged at 120,000 g for 16 hours at 4° C. (Beckman SW 65 rotor). Fractions (250 $\mu$l) were collected by piercing the bottom of the tube and assayed for RT activity. The density of the fractions was determined with a refractometer.

Electron Microscopy

Tumour tissue and monocytes from patients with breast cancer and monocytes from control subjects were fixed with cacodylate buffered glutaraldehyde (2.5% v/v), embedded in araldite, and thin-sectioned. Sections were stained with lead citrate and uranyl acetate (2% v/v). These and the resuspended pellets from CFCM were examined with a Phillips 301 electron microscope.

a. MCF7 cell line

The supernatant from MCF7 cells was assayed for RT activity.

b. U937 cell line

U937 is a non-adherent human monocyte derived continous cell line growing in standard RPMI medium. Resuspended pellets derived from monocytes of patients with breast cancer were added to flasks containing U937 and incubated for 48 hrs. The medium was then replaced and culture of the U937 cells continued. Two further changes of medium took place at weekly intervals and after a further week of culture the medium was removed, filtered through a 200 nm filter and centrifuged at 100,000 g at 4,C for o1 hr. RT assay was then performed on the pellet. Culture of the U937 cells was continued with the addition of 15 $\mu$mol/l 5'azacytidine to the medium and after a further week the medium was removed and assayed for RT activity. RT activity was also estimated on U937 cells which had not been treated with monocyte derived material.

c. Cocultivation experiments

Monocytes which were known to be RT positive were added to culture flasks containing U937 cells. The monocytes adhered to the flask and after 48 hrs incubation the U937 cells were decanted. The U937 cells were then treated as before with weekly changes of medium and after the third change of medium the medium was assayed for RT activity.

Infected U937 cells were then cocultivated with the MRC-5 cell line and after incubation decanted. Culture of the MRC-5 line was then continued as usual.

d. Pleural effusions and ascites

Pleural effusions were obtained from 5 patients with secondary breast cancer and ascitic fluid from 1 patient with secondary breast cancer. The cells were separated by centrifugation and cultured in MEM with the addition of 15 $\mu$mol 5'azacytidine. After 6 days incubation the supernatant was assayed for reverse transcriptase activity. When the cells were established as monolayers, U937 cells were added and cultured for 48 hrs. The U937 cells were then decanted, cultured and assayed for RT activity as before.

The epithelial origin of the pleural effusion cells was verified by staining with the epithelial specific monoclonal antibody CAM 5-2.

RESULTS

In the presence of 5'-azacytidine, and taking a cut-off for positivity of 15 pmol of dCTP RT activity was observed in 31 out of 32 patients with breast cancer (97%). In contrast, RT activity was detected in only 3 out of the 27 controls (11%). the mean RT activity of the CFCM from patients with breast cancer was 732 (SEM 157) pmol of dCTP incorporated/10 monocytes compared with that of control subjects, which was 6.5 (SEM 2) pmol of dCTP incorporated/10 monocytes ($p<0.0001$; Wilcoxon rank sum test, two tailed).

The RT activity detected in the CFCM was found in fractions with buoyant densities between 1.165 and 1.18 g/ml on a sucrose density gradient. This peak of activity was abolished when the CFCM was treated with Nonidet P40 and DTT before separation on the sucrose density gradient.

Monocytes from patients with breast cancer revealed retrovirus-like particles near the surface of the cells. These resembled particles seen in HT/H9 cell-line infected with human immunodeficiency virus (HIV), a typical retrovirus used for comparison. Electron microscopy of the breast cancer cells did not reveal any particles suggestive of viruses, but macrophages within the tumour contained particles similar to those observed in the incubated monocytes from patients with breast cancer and to the HIV in the infected HT/H9 cell line. Negative-stain electron microscopy of pellets obtained from CFCM from patients with breast cancer revealed the presence of envelope particles with a fringed surface resembling murine mammary tumour virus.

MCF7 cell line

RT activity was detected in low titre in the culture of MCF7 which was tested.

U937 cell line

When the supernatant from infected monocytes is added to U937 cells, these cells become producers of reverse transcriptase indicating that they have become infected with the retrovirus. These cells are modified by this infection and are no longer immortal, dying after 3–4 passages.

Cocultivation of infected monocytes with U937 also results in transfer of viral activity to the cell line. This activity is in turn transmitted to MRC-5 which continues to grow without inhibition and appears to be a stable producer of virus.

Pleural effusions and ascites 5 pleural effusions and one ascitic fluid have been cultured and assayed. Reverse transcriptase activity has been detected in the culture medium in all cases. The cells which grow are varied in appearance but stain with CAM 5-2, confirming their epithelial origin. When U937 cells are cocultivated with these cells the U937 cells become producers of reverse transcriptase indicating that they have become infected with the retrovirus from the pleural effusion.

EXAMPLE 2

Inhibition of Reverse Transcriptase Activity

Monocytes from a patient with breast cancer were incubated in Eagles medium containing 10% foetal calf serum and 1 $\mu$M of 3'-azido-3'-deoythymidine for 6 days. Cell-free culture medium was assayed for reverse transcriptase activity in accordance with the procedures described above and no activity was detected.

|  | −AZT | +AZT |
| --- | --- | --- |
| Reverse Transcriptase Activity (cpm Incorporated) | 1455 | 222 |

The following Examples are intended for illustration only and are not intended to limit the scope of the invention in any way. The term 'active ingredient' as used in the Examples means 3'-azido-3'-deoxythymidine.

EXAMPLE 3

Tablet Formulations

The following formulations A to C were prepared by wet granulation of the ingredients with a solution of povidone, followed by addition of magnesium stearate and compression.

| Formulation A | | |
|---|---|---|
| | mg/tablet | mg/tablet |
| (a) Active Ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |

| Formulation B | | |
|---|---|---|
| | mg/tablet | mg/tablet |
| (a) Active Ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (e) Magnesium Stearate | 5 | 3 |
| | 500 | 300 |

| Formulation C | |
|---|---|
| | mg/tablet |
| Active Ingredient | 100 |
| Lactose | 200 |
| Starch | 50 |
| Povidone | 5 |
| Magnesium Stearate | 4 |
| | 359 |

The following formulations, D and E, were prepared by direct compression of the admixed ingredients. The lactose used in formulation E was of the direct compression type (Diary Crest—"Zeparox").

| | mg/tablet |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation was prepared by wet granulation of the ingredients (below with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

Drug release took place over a period of about 6–8 hours and was complete after 12 hours.

EXAMPLE 4

Capsule Formulations

Formulation A

A capsule formulation was prepared by admixing the ingredients of Formulation D in Example 3 above and filling into a two-part hard gelatin capsule. Formulation B (infra) was prepared in a similar manner.

| | mg/capsule |
|---|---|
| Formulation B | |
| (a) Active Ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active Ingredient | 250 |
| (b) Macrogol 4000 BP | 350 |
| | 600 |

Capsules were prepared by melting the macrogol 4000 BP, dispersing the active ingredient in the melt and filling the melt into a two-part hard gelatin capsule.

| Formulation D | |
|---|---|
| | mg/capsule |
| Active Ingredient | 250 |
| Lecithin | 100 |
| Arachis Oil | 100 |
| | 450 |

Capsules were prepared by dispersing the active ingredient in the lecithin and arachis oil and filling the dispersion into soft, eleastic gelatin capsules.

Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 5

Injectable Formulation

| Formulation A | | |
|---|---|---|
| Active Ingredient | | 0.200 g |
| Hydrochloric acid solution, | 0.1 M q.s. to pH | 4.0 to 7.0 |
| Sodium hydroxide solution, | 0.1 M q.s. to pH | 4.0 to 7.0 |
| Sterile water | q.s. to | 10 ml |

The active ingredient was dissolved in most of the water (35°–40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

| Formulation B | |
|---|---|
| Active Ingredient | 0.125 g |
| Sterile, pyrogen-free, pH 7 phosphate buffer, q.s. to | 25 ml |

EXAMPLE 6

Intramuscular Injection

| Active Ingredient | 0.20 g |
|---|---|
| Benzyl Alcohol | 0.10 g |
| Glycofurol 75 | 1.45 g |
| Water for Injection q.s to | 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE 7

Ingredients

| Active Ingredient | 0.2500 g |
|---|---|
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water q.s. to | 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE 8

Suppository

| | mg/suppository |
|---|---|
| Active Ingredient (63 $\mu$m)* | 250 |
| Hard Fat, BP (Witepsol H15 - Dynamit NoBel) | 1770 |
| | 2020 |

*The active ingredient was used as a powder wherein at least 90% of the particles were of 63 $\mu$m diameter or less.

One-fifth of the Witepsol H15 was melted in a steam-jacketed pan at 45° C. maximum. The active ingredient was sifted through a 200 um sieve and added to the molten base with mixing, using a silverson fitted with a cutting head, until a smooth dispersion was achieved. Maintaining the mixture at 45° C., the remaining Witepsol H15 was added to the suspension and stirred to ensure a homogenous mix. The entire suspension was passed through a 250 um stainless steel screen and, with continuous stirring, was allowed to cool to 40° C. At a temperature of 38° C. to 40° C. 2.02 g of the mixture was filled into suitable plastic moulds. The suppositories were allowed to cool to room temperature.

EXAMPLE 9

Pessaries

| | mg/pessary |
|---|---|
| Active Ingredient 63 $\mu$m | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture.

We claim:

1. A method for the treatment of breast carcinoma in a human which comprises the administration of a reverse transcriptase inhibitor or a pharmaceutically acceptable derivative thereof to the human in an amount effective to treat said breast carcinoma.

2. The method according to claim 1 wherein said reverse transcriptase inhibitor is selected from the group consisting of 3'-azido purine or pyrimidine nucleosides, 2',3'-dideoxy purine nucleosides, 3'-fluoronucleosides, carbocyclic nucleosides, 2',3'-dideoxy-2',3'-didehydro nucleosides and ribavirin.

3. The method according to claim 1 wherein said reverse transcriptase inhibitor is 3'-azido-3'-deoxythymidine.

4. A method of alleviating the symptoms of human breast carcinoma which comprises the administration of a reverse transcriptase inhibitor or a pharmaceutically acceptable derivative thereof to the human in an amount effective to alleviate said symptoms.

5. A method of inhibiting the reverse transcriptase activity of retrovirus or retrovirus-like particles in monocytes containing such particles which method comprises treating such monocytes with effective amounts of 3'-azido-3'-deoxythymidine or a pharmaceutically acceptable derivative thereof.

* * * * *